United States Patent [19]

Nishizawa

[11] Patent Number: 4,814,057
[45] Date of Patent: Mar. 21, 1989

[54] ELECTROPHORETIC APPARATUS

[76] Inventor: Hideyuki Nishizawa, 1-5-1 Nakazato Kita ku, Tokyo, Japan

[21] Appl. No.: 143,546

[22] Filed: Jan. 13, 1988

[51] Int. Cl.$^4$ ............................................. G01N 27/26
[52] U.S. Cl. .................................................. 204/299 R
[58] Field of Search ......................... 204/299 R, 182.8

[56] References Cited

U.S. PATENT DOCUMENTS 3,856,656 12/1974 Brink ............................... 204/299 R
3,902,987 9/1975 Cawley ........................... 204/299 R

FOREIGN PATENT DOCUMENTS 2144057 6/1987 Japan .

Primary Examiner—John F. Niebling
Assistant Examiner—Isabelle Rodriguez
Attorney, Agent, or Firm—Donald D. Mon; David O'Reilly

[57] ABSTRACT

An open top electrode tank including two electrode chambers respectively containing an electrolyte and an electrode, and an open top cooling tank containing cooling fluid are superposed one upon the other. A separating zone is attached to the bottom of the cooling tank, and bent portions of a pair of bridging filter papers are attached to predetermined positions of a separating zone. Permanent magnets are disposed on both sides of each filter paper and on the bottom of the cooling tank for attracting each other.

9 Claims, 3 Drawing Sheets

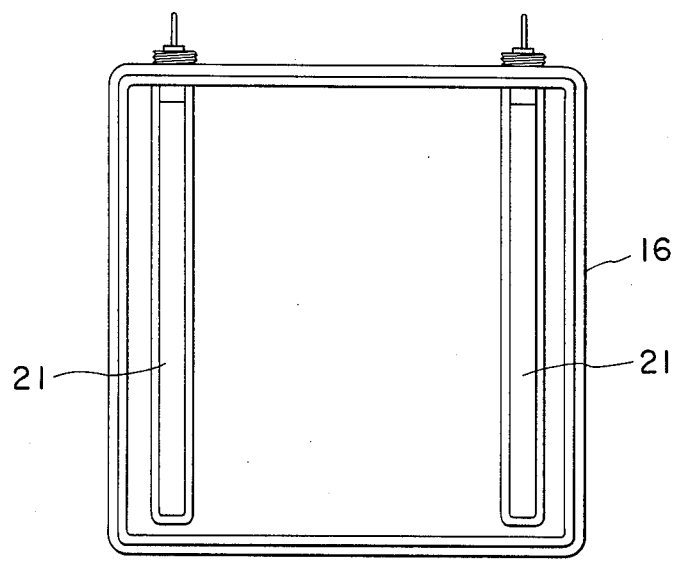
F I G. 3
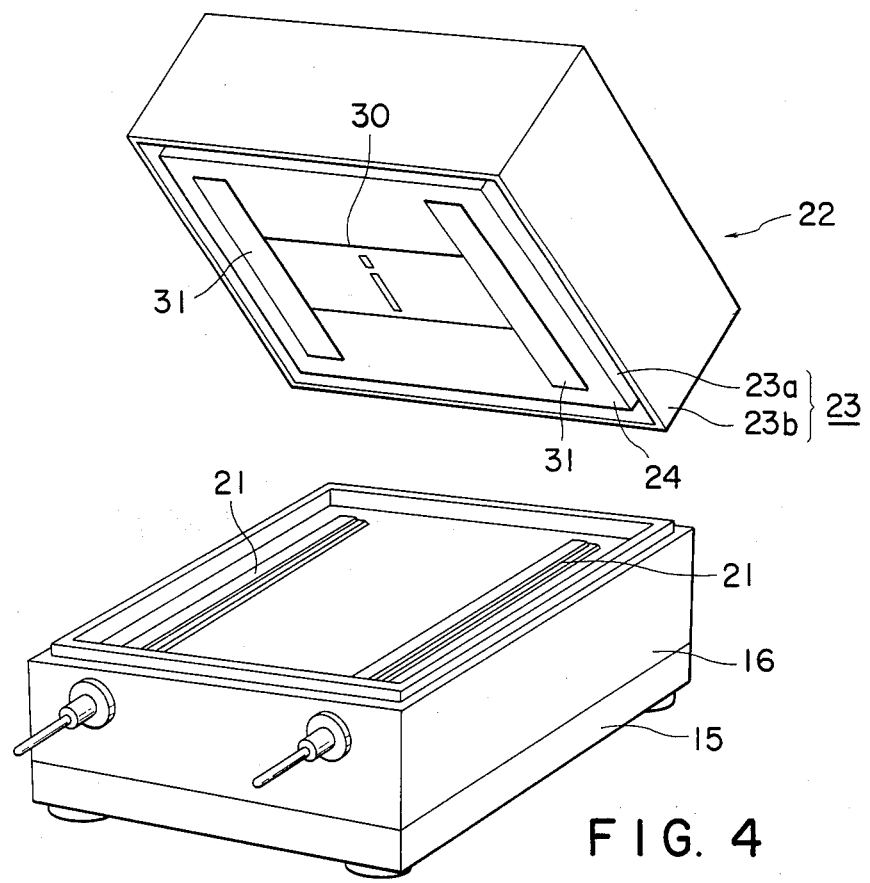
F I G. 4

ELECTROPHORETIC APPARATUS

FIELD OF THE INVENTION

This invention relates to electrophoretic apparatus that can be used either for zone electrophoresis or for isoelectric focusing.

BACKGROUND OF THE INVENTION

Methods of electrophoresis in which ionic substances are separated in a solution by using such separating carriers as paper, cellulose acetate film, starch gel, polyacrylamide gel, etc., are classified into zone electrophoresis methods and isoelectric focusing. Both of these methods have been widely used as means for separating proteins, enzymes, or the like.

A conventional electrophoretic apparatus is constituted by an electrophoretic separating part and a source part. Although the conventional electrophoretic separating part provides an excellent performance, its mechanical construction is complicated and expensive, and the electrophoretic portion cannot readily be used. Where only one sample can be separated with only one electrophoretic operation as a two dimensional electrophoresis using a combination of isoelectric focusing and carrier focusing (which became the usual practice), or where electrophoresis is required to be performed under various separating conditions, it is necessary to use a plurality of electrophoretic apparati, which is uneconomical.

The electrophoretic separating part of the electrophoretic apparatus comprises as its essential elements a separating carrier, positive and negative two electrode tanks respectively containing electrolyte, electrodes for passing electric current through solutions contained in respective tanks, and a bridge which ionically and conductively couples together the electrodes and the separating carrier, and which has a relatively simple construction.

When current is passed, the separating carrier generates heat which degrades the separation performance and denatures the separated substance so that it is necessary to provide means for cooling the separating carrier. Such cooling means not only occupies a substantial portion of the electrophoretic apparatus but also complicates its construction.

Accordingly, it is an object of this invention to provide an improved electrophoretic apparatus having a simple construction which can be formed at a low cost by simplifying the construction at the cooling means for the separating carrier.

Another object of this invention is to provide an improved electrophoretic apparatus capable of preventing condensation formed on the outer surface of a cooling tank, which cooling tank is provided for cooling the separating carrier, from invading into a gel film portion contributing to the electrophoresis. The apparatus can then be used for the zone electrophoresis and for the isoelectric focusing.

A further object of this invention is to provide a novel electrophoretic apparatus that can increase the upper limit of the applied voltage above that of any known prior art electrophoretic apparatus.

BRIEF DESCRIPTION OF THE INVENTION

According to this invention there is provided electrophoretic apparatus comprising an electrode tank with its upper surface open and having two electrode chambers partitioned by a partition wall for containing electrolyte and electrodes, and a cooling tank for containing cooling water. The cooling tank has a thin bottom plate snugly fitted in the upper opening, and a separating zone adhered to the outer surface of the bottom plate of the cooling tank. A pair of bridging filter papers are folded along their longitudinal sides. Pairs of elongated magnet members are disposed on both sides of each filter paper for securing the same to predetermined portions of the separating zone, and another pair of elongated magnet members is provided for the bottom plate of the cooling tank at positions close to the filter papers for attracting each other with the pairs of elongated magnetic members.

BRIEF DESCRIPTION OF THE DRAWINGS

In the accompanying drawing:

FIG. 3 is a bottom view showing a portion of the embodiment of FIG. 2; and

FIG. 4 is a perspective view showing the manner of using the embodiment shown in FIG. 2 for isoelectric focusing.

DESCRIPTION OF THE PREFERRED EMBODIMENT

Figure 1:
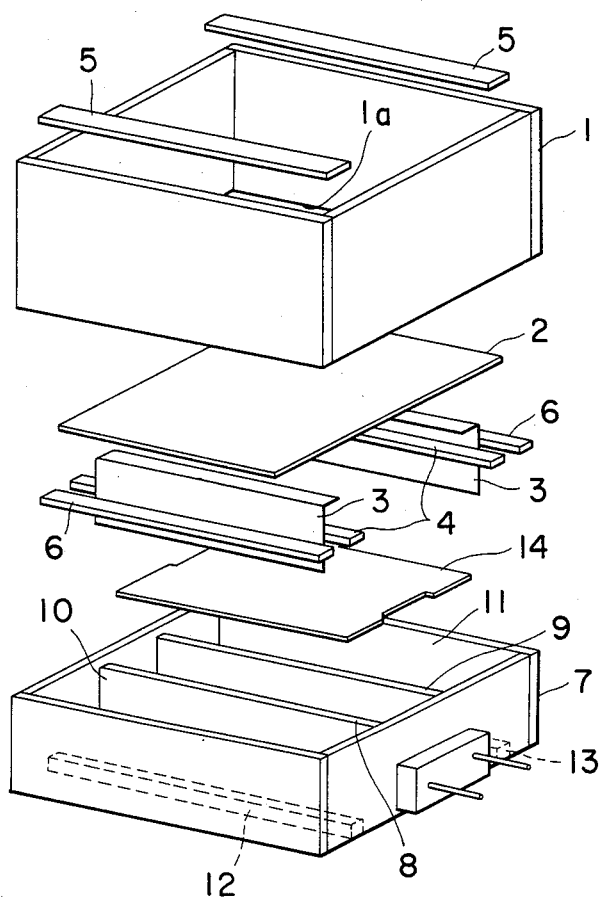
FIG. 1 is an exploded perspective view showing a first embodiment of this invention.

A first embodiment of this invention shown in FIG. 1 comprises a box shaped cooling tank with a thin bottom plate 1 made of plastic, glass or the like. Cooling tank 1 is filled with cooling water, and to the lower surface of bottom plate 1a there is secured a separating carrier made of a thin plate impregnated with a separating buffer liquid.

Bridging filter papers 3 are formed by folding inwardly longer edge portions of rectangular pieces of a suitable size. The inwardly folded edge portions of the two filter papers 3 are secured to both edge portions of the separating carrier 2.

Stripe-shaped rubber magnets 4 are disposed along the inner sides of filter papers 3, and similar stripe-shaped rubber magnets 5 are disposed along both side edges of the cooling tank 1 such that magnets 3 and 5 attract each other. Filter papers 3 are thereby secured to the separating carrier 2 by the attractive force created between the magnets 4 and 5. Further, rubber magnets 6 are disposed on the outside of the filter papers 3 such that magnets 4 and 6 attract each other. The interior of an electrode tank 7 made of insulating material such as plastic or the like is divided into positive and negative electrode chambers 10 and 11 by partition walls 8 and 9 made of insulating material. Platinum electrodes 12 and 13 are supplied with voltage from an external source, not shown. They are embedded in the bottom surfaces of the electrode chambers.

After preparing the electrophoresis part and the electrode part described above, a shielding plate 14 is mounted to close the upper opening of the electrode tank 7 to overlie both partition walls 9 and 10. Then the cooling tank 1 assembled as above described is mounted on the electrode tank 7. Then the bridging filter papers 3 depending from the separating carrier 2 are dipped into electrolyte to absorb the same, whereby a bridge interconnecting the separating carrier 2 and the electrode layer 7 is formed, thus enabling electrophoresis separation.

In the embodiment described above, because the separating carrier 2 is directly contacted by the lower surface of the bottom plate 1a of the cooling tank 1, a simple water tank can be used as the cooling means for providing sufficient cooling effect. Moreover, because the upper surface of the cooling tank 1 is open, the cooling water can evaporate and is cooled by the latent heat of evaporation. Accordingly it is possible to maintain the temperature of the cooling water near room temperature. Where it is necessary to use colder water, ice water can be used. For this reason it is not necessary to constantly circulate the cooling water as in prior art apparatus, thereby simplifying the construction.

Moreover, since each bridging filter paper is disposed between rubber magnets 4 and 6 there is no fear of elongating the paper when its folded portion is wetted by the buffer liquid. Accordingly one side of the filter paper 3 is always in close contact with the separating carrier, while the other side is held perpendicular to the separating zone.

Shielding plate 14 efficiently separates the electrolyte from the separating carrier 2, thereby preventing vapor generated by the electrolyte from condensing on the lower surface of the separating carrier 2.

In this embodiment, one or two of the stripe-shaped rubber magnets 4, 5, and 6 can be substituted by a ferromagnetic substance such as iron. Of these magnets and iron pieces, those brought into direct contact with the separating carrier or the filter paper are preferably coated with a film of a chemically stable substance so that they can be readily separated. The electrode chamber 7 may be separated by a single partition wall instead of by two partition walls 8 and 9.

Although the separating carrier can be made of various materials, it has been found that polyacrylamide gel gives a satisfactory result. A polyacrylamide gel film utilizing cores of nonwoven cloth made of polyester polyamide has been found to be most efficient. Since the gel film has a high mechanical strength it can readily be handled, and even a gel film having a thickness of less than 0.5 mm does not break. The separating performance and the separating time of this gel film are comparable with those of an ordinary polyacrylamide gel film, but as it is possible to make the gel film extremely thin as above described, it is possible to greatly reduce the time required to chemically treat the gel film such as by dyeing. This shortens the total analysis time.

The apparatus of this embodiment can be used with good results for isoelectric focusing in addition to the conventional electrophoretic separation and has performances comparable to those of a slab gel electrophoretic apparatus of more complicated construction.

As above described, the apparatus of this embodiment has a simple construction and can be manufactured at a low cost. It is superior to two dimensional electrophoresis capable of separating only one sample by one operation. The apparatus is more economical than one which requires many electrophoretic apparati wherein electrophoresis must be made under various separating conditions.

Where the apparatus of the foregoing embodiment was actually used, it was noted that there are the following problems 1. Moisture in the air condenses on the outer surface of the cooling tank 1 and the dew thus formed flows down along the outer wall of the cooling tank to enter into the gel film constituting the separating carrier 2.
2. Where the apparatus is used for isoelectric focusing instead of zone electrophoresis, a better result would be obtained when there is a lesser quantity of solution present at the electrode portion. In the apparatus of the first embodiment, the solution at the electrode portion becomes excessive, thus failing to obtain satisfactory results.
3. When used for the isoelectric focusing, since the bottom plate of the cooling tank is made of a plastic plate or a glass plate its heat conductively is relatively poor, so that its cooling efficiency is low. Thus unless the upper limit of the impressed voltage is limited to a relatively low value, the gel film can burn due to excess voltage.

The second embodiment is devised for solving these problems of the first embodiment.

Figure 2:
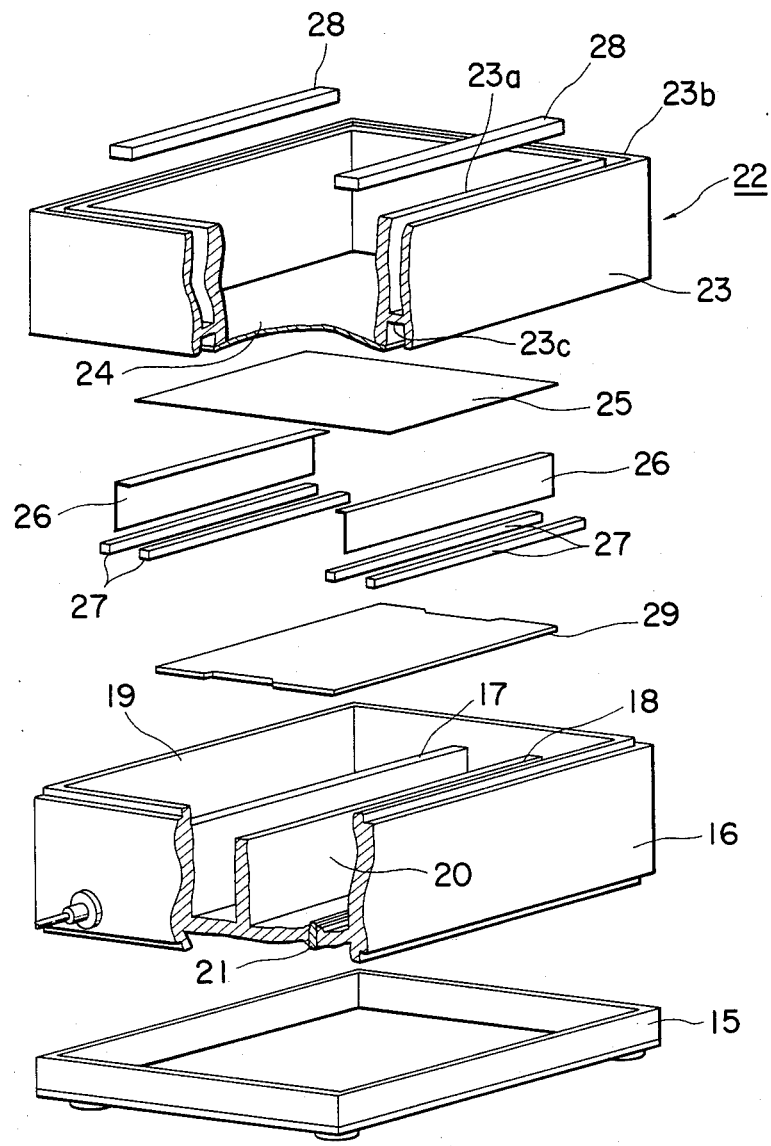
FIG. 2 is a similar view showing a second embodiment of this invention.

As shown in FIGS. 2–4, the second embodiment comprises a shallow, boxed-shaped base 15 and a box-shaped electrode tank 16 mounted thereon. The inside of the electrode tank 16, is made of insulating material such as plastic or the like, and is partitioned into three compartments by partition walls 17 and 18. Stripe-shaped platinum electrodes 21 are embedded in the bottom surface of the positive and negative electrode chambers 19 and 20 on both sides, with portions of the electrodes exposed. A cooling tank 22 comprises a side wall 23 of a double construction having a letter H shaped cross-section made up of an inner side wall 23a, an outer side wall 23b, a connecting wall 23c, and a bottom wall 24 made of such highly heat conductive material as aluminum ceramic, secured to the bottom surface of the inner wall 23a. Portions of the inner and outer side wall 23a and 23b below the connecting wall 23c are made to be much shorter that the upper portion. Spaces between partition walls 17 and 18 are present between electrode chambers 19 and 20 so that the electric insulation between the positive and negative electrode chambers is perfect.

Zone electrophoresis is performed as follows by using the apparatus of the second embodiment. Electrophoresis buffer liquid is filled in respective electrode chambers 19 and 20 of the electrode tank 16, while cooling water or ice water is filled in the cooling tank 22. Then a gel film impregnated with separating buffer liquid is bonded to bottom plate 24 of the cooling tank 22 so as to form a separating zone. A rectangular bridging filter paper 26 of a suitable size is bent along its longitudinal edge, and the bent portion is disposed close to the side wall of the electrode 21 at the lower portion of the separation zone 25.

Filter papers 26 are secured to the bottom plate 24 of the cooling tank 22 by a strip shaped rubber magnet 27 on both sides of each filter plate 24. Rubber magnets 28 are disposed on the inner surface of the bottom plate 24 to attract rubber magnets 27. Then a shielding plate 29 is placed to overlie the partition walls 17 and 18 of the electrode tank 16 and to bridge both side walls. A cooling tank 22 supporting the bridging filter papers 26 is mounted on the electrode tank 16. Then the portions from which the bridging filter papers 26 depend are brought into contact with the electrolyte in the electrode chamber so that the filter papers absorb the electrolyte to form a bridge, thereby enabling electrophoresis. Then the electrodes are connected to a source, not shown, to start electrophoresis.

When zone electrophoresis is performed by using the apparatus described above, then since the side wall 23 of the cooling tank 22 has a double wall construction and since the length of the portion beneath the connecting wall 23a between both side walls 23a and 23b is much shorter than that of the portion above the connecting wall, the following advantages can be obtained. In particular, since the side wall has a double wall construction, condensation is not formed on the outer surface of the outer wall 23b. The condensation formed on the inner surface of the inner and outer surfaces of the inner and outer side walls 23a and 23b does not flow down to the separating zone because it is intercepted by connecting wall 23c. In addition, the portions of the inner and outer side walls 23a and 23b below the connecting wall 23c have a small area. Since these portions are not directly in contact with outside air, the quantity of dew formed on these portions is small so that the electrophoresis operation is completed before the dew grows to large drops. As a consequence the dew is prevented from entering into the separating zone which otherwise could impair the electrophoresis.

Moreover, according to this invention, since highly heat conductive material such as aluminum ceramic is used for the bottom plate of the cooling tank 22, cooling is effected efficiently. As a consequence, even when a high voltage is impressed, the separating carrier does not burn.

The apparatus of the second embodiment is used for performing the electrophoresis in the following manner. As shown in FIG. 4, the electrolyte in the electrode tank 16 is removed and the electrode tank 16 is placed with its plates on the upper side. Then an elongated gel film 30 having a length corresponding to the distance between electrodes and impregnated with amphoteric electrolyte or separating electrophoresis is bonded to the bottom plate 24 of the cooling tank 22 perpendicularly to the electrodes 21. The opposite ends of the gel film 30 are bonded to rectangular filter plates 31 impregnated with an acidic or basic solution necessary for separation or removal (for the positive side, an acidic solution, or for the negative side, a basic solution).

Then the cooling tank 22 is mounted on the electrode tank 16 to contact the filter papers 31 with corresponding electrodes 21. Then the electrodes are connected to a source, not shown, for commencing the isoelectric focusing. With the modified embodiment, since the acidic and basic solutions impregnated into the filter papers are present near the electrode 21, there is no fear that the quantities of the solutions would not become excessive thus ensuring satisfactory isometric focusing. As has been stated above, there is no fear of troubles caused by condensation, or of burn out of the gel film caused by impressed voltage.

When a transparent aluminum ceramic is used for the bottom plate 24 it is possible to observe the gel film 30 from above the cooling tank 22 during the isoelectric focusing.

It should be understood that the invention is not limited to the embodiments described above. For example, the electrode 21 may be constituted by a bar made of the same material as the bottom plate of the electrode tank 16, and platinum foils or wires bonded to the upper and lower surfaces of the bar. Of course the electrode is embedded in the bottom plate. Alternatively, the electrode 21 can be made of suitable material that can withstand the electrolysis and that has sufficient electroconductivity, for example graphite. Furthermore, the electrode may be made of a metal plated with platinum. The material for constructing the bottom plate 24 of the cooling tank 24 is not limited to aluminum ceramic, so that any material having high electroconductivity can be used.

As above described with the apparatus of the second embodiment, the condensation formed on the surface of the cooling tank does not interfere with the electrophoresis. Further it can be used as either zone electrophoretic apparatus, or isoelectric focusing without adding an auxiliary device, which is economical.

What is claimed is:

1. Electrophoretic apparatus comprising:
   an open-topped electrode tank having an upper opening, a bottom, a peripheral wall and a partition means providing a pair of electrode chambers bounded by the partition means and by portions of said outer wall:
   an electrode in each chamber;
   a cooling tank for containing cool water, said cooling tank having a thin thermally conducting bottom plate snugly fitted in said upper opening, said cooling tank also having an upper opening;
   a separating zone adhered to the bottom surface of the bottom plate of said cooling tank;
   a pair of bridging filters folded to form a fold and two edges, one edge of each filter being in contact with said peripheral wall inside a respective electrode chamber, and the other edge of the filter being in contact with said separating zone;
   a first pair of magnet members in said cooling tank atop said bottom plate each opposite a respective one face of a respective filter;
   a second pair of magnet members in said electrode tank each opposite a respective one face of a respective filter and in alignment with respective ones of said first magnet members, whereby said filters are secured to separated portions of said separating zone.

2. Electrophoretic apparatus according to claim 1 in which a third pair of magnet members is disposed outside of said peripheral wall, each opposite a respective other said face of said filters and in alignment with a respective one of each of said second magnet members to secure said other faces of the filters to said peripheral wall in a respective chamber.

3. Electrophoretic apparatus according to claim 1 wherein a portion of the electrode disposed in each electrode chamber is exposed to the inside and outside surfaces of the bottom plate of said electrode tank, in which said cooling tank is provided with an inner wall, an outer wall and a connecting wall interconnecting said inner and outer walls, thus forming a double wall construction having the form of a letter H in cross-section, and wherein the bottom wall of said cooling tank is made of a material having a high heat conductivity.

4. Electrophoretic apparatus according to claim 1 wherein portions of the inner and outer side walls of said cooling tank located below said interconnecting wall are shorter than portions above said interconnecting wall, and in which the bottom plate of said cooling tank is made of highly heat conductive material.

5. Electrophoretic apparatus according to claim 1 wherein the base plate of said cooling tank is made of aluminum ceramic.

6. Electrophoretic apparatus according to claim 1 wherein each electrode is entirely made of platinum.

7. Electrophoretic apparatus according to claim 1 wherein each electrode comprises a bar made of the same material as the base plate of said electrode tank and a platinum foil or platinum wire bonded to the opposite surfaces of said bar.

8. Electrophoretic apparatus according to claim 1 wherein each electrode comprises a bar of metal other than platinum, which metal is plated with platinum.

9. Electrophoretic apparatus according to claim 1 wherein each electrode is made of graphite.

* * * * *